(12) United States Patent
Abe et al.

(10) Patent No.: US 8,828,732 B2
(45) Date of Patent: Sep. 9, 2014

(54) METHOD OF LABELING SUGAR CHAIN

(75) Inventors: Midori Abe, Tokyo (JP); Hideyuki Shimaoka, Tokyo (JP); Hiromitsu Kuramoto, Tokyo (JP)

(73) Assignee: Sumitomo Bakelite Co., Ltd., Tokyo (JP)

( * ) Notice: Subject to any disclaimer, the term of this patent is extended or adjusted under 35 U.S.C. 154(b) by 375 days.

(21) Appl. No.: 12/989,717

(22) PCT Filed: Apr. 28, 2009

(86) PCT No.: PCT/JP2009/001927
§ 371 (c)(1),
(2), (4) Date: Oct. 26, 2010

(87) PCT Pub. No.: WO2009/133696
PCT Pub. Date: Nov. 5, 2009

(65) Prior Publication Data
US 2011/0046364 A1   Feb. 24, 2011

(30) Foreign Application Priority Data
Apr. 30, 2008  (JP) ................................. 2008-118429

(51) Int. Cl.
G01N 33/00 (2006.01)
C07H 1/06 (2006.01)
C07H 1/00 (2006.01)
C08B 37/00 (2006.01)

(52) U.S. Cl.
USPC ................... 436/94; 436/93; 436/91; 73/866; 536/55.3; 536/124; 536/127

(58) Field of Classification Search
CPC ............. C07H 1/06; C07H 5/06; G01N 33/02
USPC .......... 436/94, 93, 91; 73/866; 536/55.3, 124, 536/127
See application file for complete search history.

(56) References Cited

U.S. PATENT DOCUMENTS

| 4,975,533 A | 12/1990 | Kondo et al. |
| 7,985,874 B2 | 7/2011 | Nishimura et al. |
| 2006/0188996 A1 | 8/2006 | Nishimura et al. |
| 2008/0254998 A1 | 10/2008 | Nishimura et al. |
| 2009/0306291 A1 | 12/2009 | Shimaoka et al. |

FOREIGN PATENT DOCUMENTS

| EP | 0 867 722 | * 9/1998 | ............ G01N 33/58 |
| JP | 64-10177 | 1/1989 | |
| JP | 7-252288 | 10/1995 | |
| JP | 10-267931 | 10/1998 | |
| WO | 2004/058687 | 7/2004 | |
| WO | 2005097844 A1 | 10/2005 | |
| WO | 2006/030584 | 3/2006 | |
| WO | 2008/018170 | 2/2008 | |

OTHER PUBLICATIONS

Supplementary European Search Report for Application No. EP 09 73 8633 dated May 16, 2011.
Xiaoyu Chen, et al., "Analysis of N-glycans from recombinant immunoglobulin G by on-line reversed-phase high-performance liquid chromatography/mass spectrometry", Analytical Biochemistry, Academic Press Inc., New York, vol. 370, No. 2, Oct. 1, 2007, pp. 147-161 (XP022278421).
Markus Pauly, et al., "Improved protocol for the formation of N-(p-nitrobenzyloy)aminoalditol derivatives of oligosaccharides", Carhohydrate Research, GB, vol. 282, No. 1, Feb. 28, 1996, pp. 1-12 (XP004018764).
Joanne Charlwood, et al., "Analysis of N-linked oligosaccharides: process towards the characterization of glycoprotein-linked carbohydrates", Biomolecular Engineering, New York, NY, US, vol. 18, No. 5, Nov. 1, 2001, pp. 229-240 (XP004308888).
International Search Report for Application No. PCT/JP2009/001927 dated Aug. 11, 2009.
Japanese Office Action, issued in corresponding Application No. JP 2010-510036, dated Oct. 22, 2013.

* cited by examiner

*Primary Examiner* — Christine T Mui
(74) *Attorney, Agent, or Firm* — Smith, Gambrell & Russell LLP

(57) ABSTRACT

The method of labeling a sugar chain from a biological sample employs a single reaction vessel for the sequential performance of the following steps of (a) isolating a sugar chain from a sample using a sugar-trapping substance; (b) washing the sugar-trapping substance having the sugar chains trapped thereon; (c) releasing the sugar chain from the sugar-trapping substance; and (d) labeling the released sugar chain with UV/visible or fluorescent compound having an amino group forming a stable labeled sugar in fewer steps than a conventional ion exchange based technique.

12 Claims, 1 Drawing Sheet

METHOD OF LABELING SUGAR CHAIN

TECHNICAL FIELD

The present invention relates to a method of efficiently isolating and labeling a sugar chain contained in a biological sample.

BACKGROUND ART

Biopolymers such as sugar chain, glycoprotein, glycopeptide, peptide, oligopeptide, protein, nucleic acid, lipid and so forth have key roles in the field of biotechnology including medical science, cell engineering, organ engineering and so forth, so that it has been understood that elucidation of mechanisms of control of biological reactions by these substances may contribute to advancement in the field biotechnology.

Among others, sugar chain is a group of substances highly versatile, and correlated to various functions owned by naturally-occurred lives. The sugar chain often exists in vivo in a form of glycoconjugate while being bound with protein and lipid, known as one of important constituents of biological body. It has increasingly been made clear that the sugar chain is deeply correlated to in vivo regulation of intercellular communication, and function and interaction of proteins.

Note that the sugar chain herein is a general term for molecules configured by monosaccharides such as glucose, galactose, mannose, fucose, xylose, N-acetylglucosamine, N-acetylgalactosamine and sialic acid, or derivatives of these monosaccharides, bound with each other via glycosidic bonds to give a chain.

Biopolymers having the sugar chain may be exemplified by proteoglycans composing plant cells contributive to stabilization of the cells; glycolipids affective to differntiation, proliferation, adhesion, migration and so forth of cells; and glycoproteins correlated to intercellular interaction and cell recognition. Mechanisms of sophisticated and precise control of the sugar chain contained in these biopolymers, based on functional substitution, assistance, amplification, regulation or inhibition with respect to the biopolymers, have increasingly been made clear. If correlations of the sugar chain with differentiation, proliferation, cell adhesion, immunity and neoplastic transformation are further revealed, it is expected to carry out new development by linking this sugar chain engineering to medical science, cell engineering or organ engineering.

In glycoprotein drugs, the sugar chain often plays an important role typically in expression of bioactivity. Accordingly, evaluation of the sugar chain, as a parameter of quality control of the glycoprotein drugs, is extremely important. In particular in the field of antibody drugs, since it was reported that structure of the sugar chain determines antibody dependent cellular cytotoxicity (ADCC activity), the structural analysis of the sugar chain has increasingly added its importance.

Accordingly, techniques of analyzing the sugar chain structure in a rapid, simple and precise manner have recently been desired, and the sugar chain analyses are conducted by a wide variety of methods including high-performance liquid chromatography (HPLC), nuclear magnetic resonance, capillary electrophoresis (CE method), mass analysis, lectin array method and so forth.

For the sugar chain analyses making use of these techniques, it is necessary to preliminarily isolate and purify the sugar chain from proteins, peptides, lipids, nucleic acids and so forth contained in a biological sample. Although HPLC and CE have widely been adopted by virtue of their excellent resolution, good reproducibility, good quantification, and high sensitivity, it is necessary to preliminarily label the reducing end of the sugar chain typically by reductive amination, for the purpose of obtaining high sensitivity. Such purification and labeling of the sugar chain however, requires time and numbers of processes, so that it is difficult to prepare a large amount of samples at a time.

A technique of solving the above-described problem may be exemplified by a method of preparing a sample embodied by using a specific sugar-trapping substance, typically described in Patent Document 1.

[Patent Document 1] WO 2008/018170

DISCLOSURE OF THE INVENTION

As described in the above, the isolation, purification and labeling of the sugar chain requires time and numbers of processes. While techniques making use of ion exchange resin, reverse-phase chromatography, activated carbon, gel filtration chromatography and so forth have been adopted to isolation and purification of the sugar chain, these techniques for isolation are not designed to specifically recognizing sugar. Therefore, incorporations of impurities (peptides, proteins or the like) are unavoidable. Also, variation of the recovery ratio often occurs by structure of the sugar chain. In addition, for the labeling of the sugar chain, it is also necessary to thoroughly dry the sugar chain obtained after the purification process, so that it takes several days to complete a series of operations from purification to labeling.

It is an object of the present invention to provide a method of purifying a sugar chain from a biological sample, and labeling it, in a simple way.

The present invention is as follows.

(1) A method of labeling a sugar chain, used for labeling a sugar chain contained in a biological sample, comprising:
(a) trapping a sugar chain in a sugar-trapping substance, which is a substance for specifically trapping a sugar chain from a biological sample;
(c) releasing the sugar chain from said sugar-trapping substance; and
(d) labeling the released sugar chain, wherein the processes (a), (c) and (d) are conducted sequentially in a single reaction vessel.

(2) A method of labeling a sugar chain, used for labeling a sugar chain contained in a biological sample, comprising:
(a) trapping a sugar chain in a sugar-trapping substance, which is a substance for specifically trapping a sugar chain from a biological sample;
(b) washing said sugar-trapping substance having the sugar chains trapped thereon;
(c) releasing the sugar chain from said sugar-trapping substance; and
(d) labeling the released sugar chain,
wherein the processes (a), (b), (c) and (d) are conducted sequentially in a single reaction vessel.

(3) The method of labeling a sugar chain as described in (1) or (2), wherein in the process (a), the sugar-trapping substance is a carrier having a functional group capable of specifically reacting with an aldehyde group of the sugar chain.

(4) The method of labeling a sugar chain as described in (3), wherein the functional group is a hydrazide group or an aminoxy group.

(5) The method of labeling a sugar chain as described in (4), wherein the sugar-trapping substance has a crosslinking polymer structure represented by the following (formula 1):

[Chemical Formula 1]

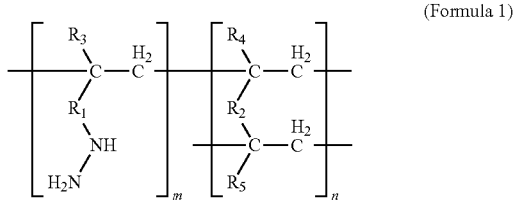

(Formula 1)

(Each of $R_1$ and $R_2$ represents a hydrocarbon chain having 1 to 20 carbon atoms which may be interrupted with —O—, —S—, —NH—, —CO— or —CONH—; each of $R_3$, $R_4$ and $R_5$ represents H, $CH_3$, or a hydrocarbon chain having 2 to 5 carbon atoms. Each of m and n represents the number of monomer units.)

(6) A method of labeling a sugar chain as described in (5), wherein the sugar-trapping substance has a crosslinking polymer structure represented by the following (formula 2):

[Chemical Formula 2]

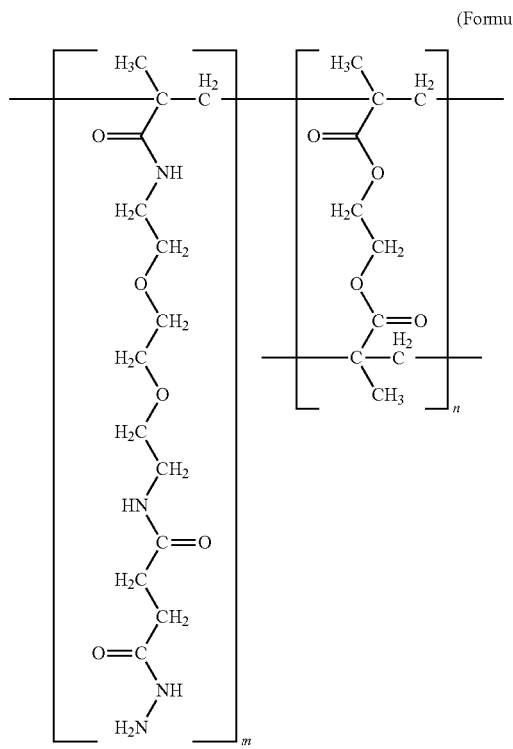

(Formula 2)

(Each of m and n represents the number of monomer units.)

(7) The method of labeling a sugar chain as described in any one of (1) to (6), wherein the process (c) has a process of applying acid treatment to said sugar-trapping substance.

(8) The method of labeling a sugar chain as described in any one of (1) to (7), wherein the processes (a) and (c) include a process of evaporating a reaction solvent.

(9) The method of labeling a sugar chain as described in any one of (1) to (8), wherein in the processes (d), the sugar chain is labeled using a compound having amino group.

(10) The method of labeling a sugar chain as described in (9), wherein labeling of the sugar chain with the compound having amino group is carried out by reductive amination.

(11) The method of labeling a sugar chain as described in (9) or (10), wherein the compound having amino group has UV-visible absorption characteristics or fluorescent characteristics.

(12) The method of labeling a sugar chain as described in any one of (9) to (11), wherein the compound having amino group is at least one selected from 8-aminopyrene-1,3,6-trisulfonate, 8-aminonaphthalene-1,3,6-trisulphonate, 7-amino-1,3-naphtalenedisulfonic acid, 2-amino-9(10H)-acridone, 5-aminofluorescein, dansyl ethylenediamine, 2-aminopyridine, 7-amino-4-methylcoumarine, 2-aminobenzamide, 2-aminobenzoic acid, 3-aminobenzoic acid, 7-amino-1-naphthol, 3-(acetylamino)-6-aminoacridine, 2-amino-6-cyanoethylpyridine, ethyl p-aminobenzoate, p-aminobenzonitrile, and 7-aminonaphthalene-1,3-disulfonic acid.

(13) A method of detecting a sugar chain comprising:
detecting a sugar chain labeled by the method of labeling a sugar chain described in any one of (1) to (12).

(14) A method of fractionating a sugar chain comprising:
fractionating a sugar chain labeled by the method of labeling a sugar chain described in any one of (1) to (12).

According to the method of labeling a sugar chain of the present invention, purification and labeling of a target compound such as sugar chain contained in a biological sample may be allowed to proceed in a single reaction vessel, and thereby the target compound may be labeled in a simple manner. Also labeling with an amino compound, which is generally adopted to analyses by HPLC, CE and so forth, may be simplified.

BRIEF DESCRIPTION OF THE DRAWINGS

The above and other objects, features and advantages of the present invention will be more apparent from the following description of certain preferred embodiments taken in conjunction with the accompanying drawings.

BEST MODES FOR CARRYING OUT THE INVENTION

Figure 1:
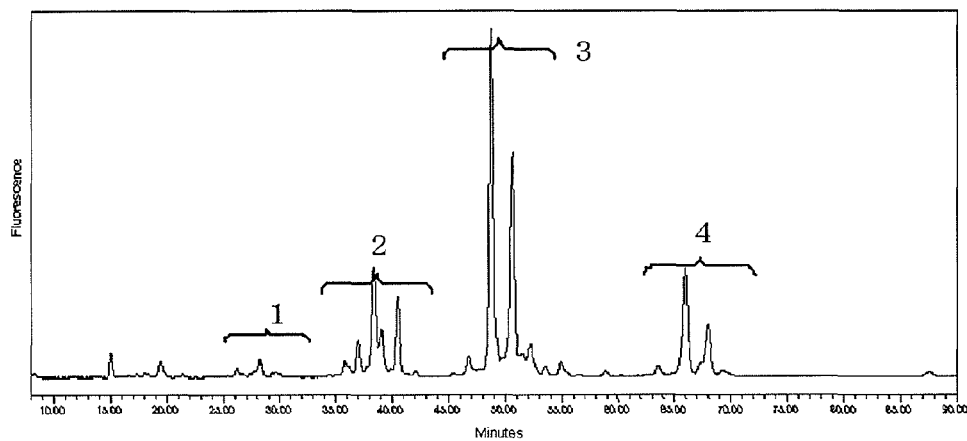
FIG. 1 is a chart illustrating a result of 2-AB labeled sugar chain of bovine fetuin obtained in Exemplary example 1, which was measured by high-performance liquid chromatography.

The present invention relates to a method of labeling a sugar chain, used for labeling a sugar chain contained in a biological sample, including:

(a) trapping a sugar chain in a sugar-trapping substance, which is a substance for specifically trapping a sugar chain from a biological sample;

(b) washing the sugar-trapping substance having the sugar chains trapped thereon;

(c) releasing the sugar chain from the sugar-trapping substance; and (d) labeling the released sugar chain, wherein the processes (a), (b), (c) and (d) are conducted sequentially in a single reaction vessel.

In the process (a), the substance for specifically trapping a sugar chain preferably has a functional group for reacting with an aldehyde group of the sugar chain. The functional group is more preferably a hydrazide group or oxylamino group.

As this sort of sugar-trapping substance, a crosslinking polymer having a structure represented by the following (formula 1) or (formula 2) is preferably used in a form of carrier.

[Chemical Formula 3]

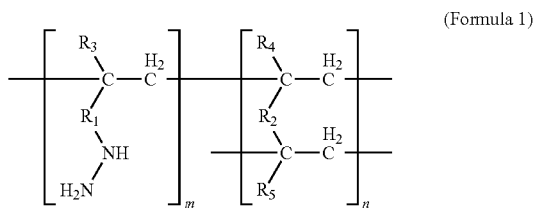

(Formula 1)

(Each of $R_1$ and $R_2$ represents a hydrocarbon chain having 1 to 20 carbon atoms which may be interrupted with —O—, —S—, —NH—, —CO— or —CONH—; each of $R_3$, $R_4$ and $R_5$ represents H, $CH_3$, or a hydrocarbon chain having 2 to 5 carbon atoms. Each of m and n represents the number of monomer units.)

$R_1$ represents a hydrocarbon chain having 1 to 20 carbon atoms which may be interrupted with —O—, —S—, —NH—, —CO— or —CONH—, and may be exemplified by the followings. Note that each of a, b and d in the formulae represents an integer of 1 to 5, and c represents an integer of 1 to 10.

[Chemical Formula 4]

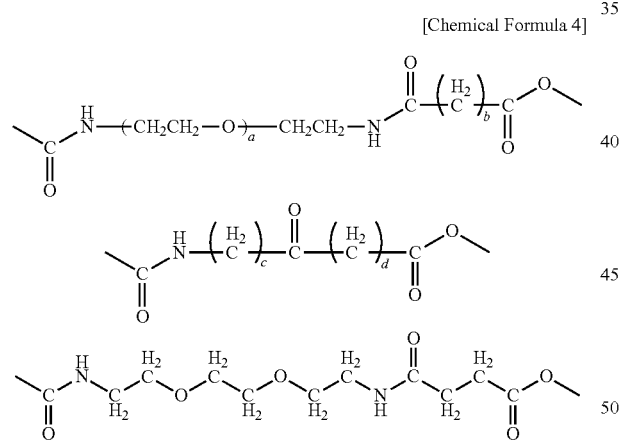

$R_2$ represents a hydrocarbon chain having 1 to 20 carbon atoms which may be interrupted with —O—, —S—, —NH—, —CO— or —CONH—, and may be exemplified by the followings. Note that each of e and f in the formulae represents an integer of 1 to 5, and g represents an integer of 1 to 10.

[Chemical Formula 5]

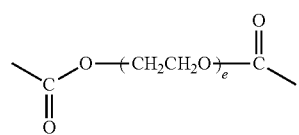

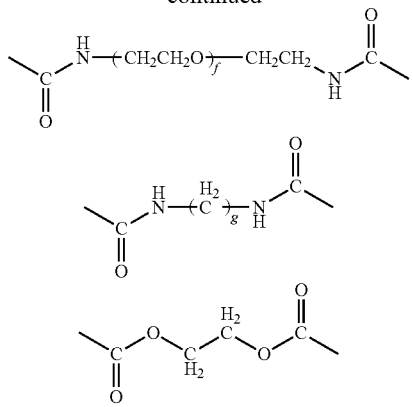

$R_3$, $R_4$ and $R_5$ may be same, or different from each other, each of which represents H, $CH_3$ or a hydrocarbon chain having 2 to 5 carbon atoms, as exemplified below. In the following formula, h represents an integer of 1 to 4.

[Chemical Formula 6]

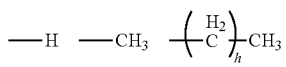

Among those represented by this (formula 1), especially preferable substance A may be exemplified by those having a crosslinking polymer structure represented by the following (formula 2).

[Chemical Formula 7]

(Formula 2)

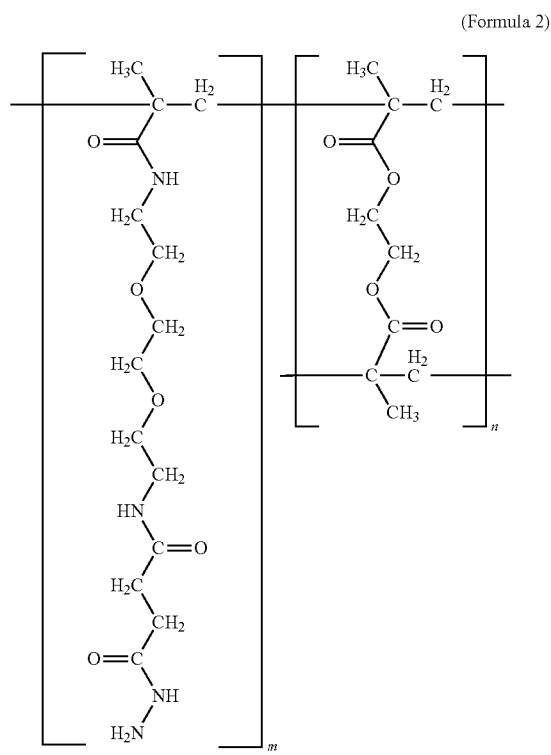

(Each of m and n represents the number of monomer units.)

Also other commercially-available, crosslinked particles containing hydrazide group, such as Affigel Hz (from BIO-RAD, 153-6047), CarboLink (™) Coupling Gel (from PIERCE, 20391), and UltraLink(R) Hydrazide Gel (from PIERCE, 53149), may be used.

As the sugar-trapping substance, also crosslinking polymers represented by the following (formulae 5) or (formula 6) may be used as carrier.

[Chemical Formula 8]

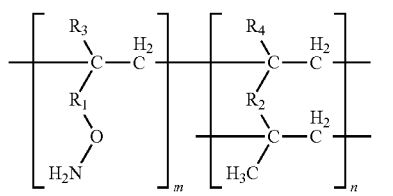

(Formula 5)

(Each of $R_1$ and $R_2$ represents a hydrocarbon chain having 1 to 20 carbon atoms which may be interrupted with —O—, —S—, —NH—, —CO— or —CONH—; and each of $R_3$, $R_4$ and $R_5$ represents H, $CH_3$, or a hydrocarbon chain having 2 to 5 carbon atoms. Each of m and n represents the number of monomer units). Specific examples of $R_1$ to $R_5$ may be exemplified by those similar to those exemplified in the explanation in relation to the (formula 1).

Still alternatively, as the polymer particle represented by the (formula 5), also a polymer particle having a structure represented by following (formula 6) may preferably be used.

[Chemical Formula 9]

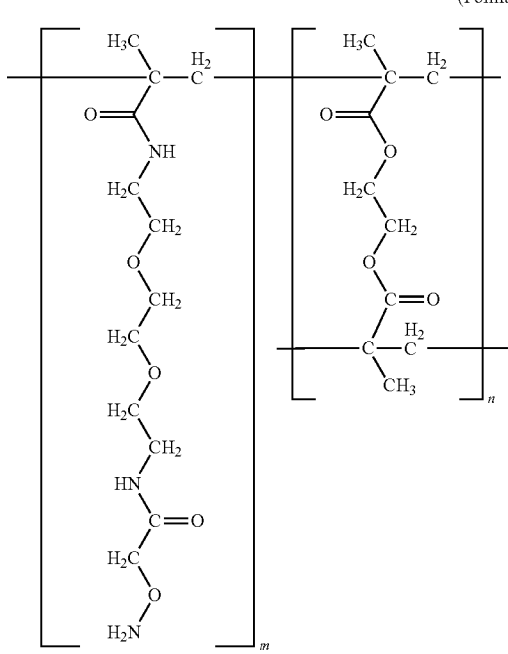

(Formula 6)

(Each of m and n represents the number of monomer units.)

Among these sugar-trapping substances, the substances having a hydrazide group may preferably be used.

In a reaction system, allowing therein the sugar chain and the sugar-trapping substance to react with each other, pH is preferably in an acidic condition, preferably 2 to 9, more preferably 2 to 7, and still more preferably 2 to 6. Reaction temperature is preferably is 4 to 90 degrees C., more preferably 25 to 90 degrees C., and still more preferably 40 to 90 degrees C. Reaction time is 10 minutes to 24 hours, preferably 10 minutes to 8 hours, and more preferably 10 minutes to 2 hours. From the viewpoint of allowing the trapping reaction of sugar chain to efficiently proceed, it may be preferable to proceed the reaction in an open system and to thoroughly vaporize the solvent.

Next, in the process (b), the sugar-trapping substance having the sugar chain trapped thereon in the process (a) is washed, so as to remove a portion of the sugar chain not trapped by the sugar-trapping substance and other biological samples. Solvents used for washing of the sugar-trapping substance include solution of a protein denaturating agent such as aqueous solution of guanidine or detergent; alcohols such as methanol, ethanol, water, and water-base buffer. For the case where aqueous solution is used for washing, pH of the aqueous solution is preferably near neutral, preferably 4 to 10, and more preferably 6 to 8.

The washing process (b) may be not conducted, depending on initial states of the biological sample, such as an amount of co-existence of substances other than the sugar chain.

In the process (c), the sugar chain is released from the sugar-trapping substance having the sugar chain trapped thereon. That is, a reaction of cutting the sugar chain out from the sugar-trapping substance is carried out. In this process, the sugar-trapping substance is preferably applied to acid treatment using a mixed solvent of acid and organic solvent, or a mixed solvent of acid and water and organic solvent. In the mixed solvent of acid and water and organic solvent, the water content is preferably 0.1% to 90%, more preferably 0.1% to 80%, and still more preferably 0.1% to 50%. A water-base buffer may be contained in place of water. Concentration of the buffer is preferably 0.1 mM to 1 M, more preferably 0.1 mM to 500 mM, and still more preferably 1 mM to 100 mM. pH of the reaction solution is preferably 2 to 9, more preferably 2 to 7, and still more preferably 2 to 6. The acid preferably adoptable herein may be exemplified by acetic acid, formic acid, trifluoroacetic acid, hydrochloric acid, citric acid, phosphoric acid and sulfuric acid; more preferably exemplified by acetic acid, formic acid, trifluoroacetic acid and phosphoric acid; and still more preferably exemplified by acetic acid and trifluoroacetic acid. Reaction temperature is preferably 4 to 90 degrees C., more preferably 25 to 90 degrees C., and still more preferably 40 to 90 degrees C. Reaction time is 10 minutes to 24 hours, preferably 10 minutes to 8 hours, and more preferably 10 minutes to 3 hours. From the viewpoint of carrying out the reaction for releasing the sugar chain efficiently proceed, the reaction may preferable be carried out in an open system to evaporate the solvent perfectly.

Since the reaction of cutting the sugar chain may be proceeded under weakly-acidic to nearly-neutral conditions, to induce hydrolysis of sugar chain or the like such as elimination of sialic acid residue or the like can be suppressed, as compared with conventional strong acid treatment such as using a cutting reaction under the presence of a strong acid such as 10% trifluoroacetic acid.

In the process (d), the free sugar chain obtained in the process (c) is labeled. The method of labeling is preferably a reaction of labeling of the sugar chain by using a compound having amino group, such as reductive amination with an arbitrary amino compound. In the reaction system, pH is preferably in an acidic to neutral condition, preferably 2 to 9, more preferably from 2 to 8, and still more preferably from 2 to 7. Reaction temperature is preferably 4 to 90 degrees C., more preferably 25 to 90 degrees C., and still more preferably 40 to 90 degrees C. Concentration of the amino compound is preferably 1 mM to 10 M. Concentration of a reducing agent is preferably 1 mM to 10 M. Reaction time is 10 minutes to 24 hours, preferably 10 minutes to 8 hours, and more preferably 10 minutes to 3 hours.

The compound having amino group preferably has UV-visible absorption characteristics or fluorescent characteristics, and is preferably at least one selected from the group as following:

8-aminopyrene-1,3,6-trisulfonate, 8-aminonaphthalene-1, 3,6-trisulphonate, 7-amino-1,3-naphtalenedisulfonic acid, 2-amino-9(10H)-acridone, 5-aminofluorescein, dansyl ethylenediamine, 2-aminopyridine, 7-amino-4-methylcoumarine, 2-aminobenzamide, 2-aminobenzoic acid, 3-aminobenzoic acid, 7-amino-1-naphthol, 3- (acetylamino) -6-aminoacridine, 2-amino-6-cyanoethylpyridine, ethyl p-aminobenzoate, p-aminobenzonitrile, and 7-aminonaphthalene-1,3-disulfonic acid.

In particular, for the case where the amino compound is a 2-aminobenzamide, pH is in an acidic to neutral condition, preferably 2 to 9, more preferably 2 to 8, and still more preferably 2 to 7. Reaction temperature is 4 to 90 degrees C., preferably 30 to 90 degrees C., and more preferably 40 to 80 degrees C. Concentration of amino compound is 1 mM to 10 M, preferably 10 mM to 10 M, and more preferably 100 mM to 1 M. Concentration of reducing agent is 1 mM to 10 M, preferably 10 mM to 10 M, and more preferably 100 mM to 2 M. Reaction time is 10 minutes to 24 hours, preferably 10 minutes to 8 hours, and more preferably 1 hour to 3 hours.

The reducing agent adoptable herein includes sodium cyanoborohidride, methylamine borane, dimethylamine borane, trimethylamine borane, picoline borane and pyridine borane, wherein sodium cyanoborohydride may preferably be used in view of reactivity.

Since the solution obtained after the process (d) contains the labeled sugar chain, unreacted portion of the excessively-added amino compound, and the reducing agent, so that a process of removing the excessive reagents is preferably carried out. All of removal using a silica column, removal by gel filtration and removal using ion exchange resin may be adoptable, wherein the solvent used therefor is preferably neutral in view of preventing elimination of sialic acid.

While the method of labeling a sugar chain has been explained in the above, according to another aspect of the present invention, there is provided a method of detecting sugar chain which includes a process of detecting a sugar chain labeled by the method of labeling a sugar chain. According to still another aspect of the present invention, there is also provided a method of fractionating a sugar chain which includes a process of fractionating a sugar chain labeled by the method of labeling a sugar chain.

While the technique of trapping a sugar chain described in Patent Document 1 adopts, in a process of labeling a trapped sugar chain, a technique of labeling based on an exchange reaction under addition of an excessive amount of a reagent, the present invention adopts a technique of labeling based on reductive amination. The reductive amination is a generally adopted method, but usually takes a long time for isolation, desalting and drying of sugar chain. The present invention makes it possible to conveniently use the reductive amination, by combining it with trapping and isolation on a carrier. The labeling based on reductive amination is advantageous over the technique of labeling described in Patent Document 1, in that (1) since the reaction is adoptable to labeling compound such as 2-aminobenzamide and 2-aminopyridine, having been adopted in general, so that previous findings obtained by using these labels may be referred to; and in that (2) bond between the sugar chain and the labeling compounds is more stable, and may therefore be storable for a long period.

EXAMPLES

The present invention will be explained referring to Examples which include the following exemplary experiments. The present invention is, however, not limited to the Model Experiments.

In this exemplary embodiment, a method of preparing, as analytical samples, sugar chains of bovine serum fetuin and bovine serum IgG, both of which are glycoproteins, and a method of analyzing them will be explained as model cases.

Exemplary Experiment 1

(Pretreatment of Biological Sample)

One milligram of bovine serum fetuin was dissolved in 50 μL of a 100 mM ammonium bicarbonate, added with 5 μL of 120 mM DTT (dithiothreitol) to react at 60 degrees C. for 30 minutes. After completion of the reaction, the mixture was added with 10 μL of 123 mM IAA (iodoacetamide), to react in darkness at room temperature for one hour. The mixture was then adapted to protease treatment using 400 U of trypsin, to thereby fragmentate the protein portion into peptides. The reaction solution was treated at 90 degrees C. for 5 minutes, and then treated using 5 U of glycosidase F, so as to release the sugar chains from the peptides, to thereby obtain a pretreated biological sample.

(Sugar Chain Trapping Process (a) and Washing Process (b))

To a disposable column containing 5 mg of beads having hydrazide group (BlotGlyco(R), from Sumitomo Bakelite Co., Ltd., BS-45601S, a polymer having a structure represented by the formula 2, with a ratio of employed monomers m:n of 20:1), which is a carrier for trapping the sugar chains, 20 μL of suspension of the pretreated biological sample and 180 μL of a 2% acetic acid/acetonitrile solution were added and reacted at 80 degrees C. for one hour. The reaction was carried out in an open system. It was visually confirmed that the solvent was completely evaporated to place the beads in the dryness state. The beads was then washed with guanidine solution, water, methanol and triethylamine solution, followed by adding 10% acetic anhydride/methanol and reacting at room temperature for 30 minutes, so as to cap the unreacted hydrazide groups. After the capping, the beads were washed with methanol, aqueous hydrochloric acid solution, and water.

(Sugar Chain Releasing Process (c))

To a disposable column containing the beads, 20 μL of ultrapure water and 180 μL of a 2% acetic acid/acetonitrile solution were added and reacted at 60 degrees C. for 2 hours. The reaction was carried out in an open system. It was visually confirmed that the solvent was completely evaporated to place the beads in the dryness state.

(Labeling Process (d))

To a disposable column containing the beads, 50 μL of a solution prepared by dissolving 2-aminobenzamide (2-AB) and sodium cyanoborohydride in a 30% acetic acid/DMSO mixed solvent so as to adjust the final concentrations thereof to 0.35 M and 1 M, respectively was added and reacted at 60 degrees C. for 2 hours.

The above-described sugar chain trapping process (a), the washing process (b), the sugar chain releasing process (c), and the labeling process (d) were conducted inside the disposable column that is a single reaction vessel.

(Process of Removing Excessive Reagent)

50 µL of the reaction solution was recovered, diluted tenfold with acetonitrile, and placed on a column packed with silica gel (Iatrobeads, 6RS-8060, from Mitsubishi Kagaku Iatron, Inc.), to thereby allow the silica gel to adsorb the labeled sugar chain. After the column was washed with acetonitrile and an acetonitrile/water mixed solution (95:5), the labeled sugar chain was recovered with 50 µL of ultrapure water.

(Detection of Labeled Sugar Chain)

The obtained sugar chain was measured by HPLC, using an amino column (Shodex Asahipak NH2P-50) at an excitation wavelength of 330 nm, and a phosphorescence wavelength of 420 nm. Results of measurement are illustrated in FIG. 1. The sugar chain labeled with 2AB was detected.

In FIG. 1, peaks 1 represent the peak derived from sugar chain containing one sialic acid, peaks 2 represent the peak derived from sugar chain containing two sialic acids, peaks 3 represent the peak derived from sugar chain containing three sialic acids, and peaks 4 represent the peak derived from sugar chain containing four sialic acids.

Exemplary Experiment 2

Figure 2:
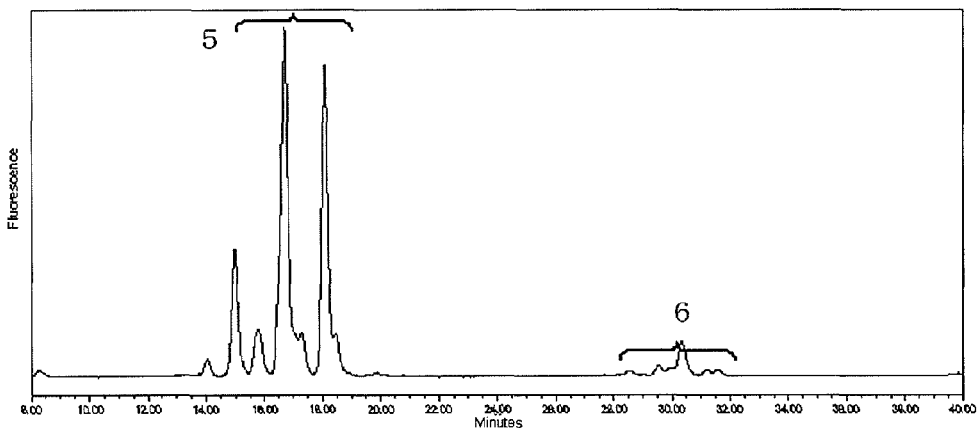
FIG. 2 is a chart illustrating a result of 2-AB labeled sugar chain of bovine serum IgG obtained in Exemplary example 2, which was measured by high-performance liquid chromatography.

The exemplary experiment 2 was conducted similarly to the exemplary experiment 1, except that bovine serum IgG was used in place of bovine serum fetuin. Results of measurement are illustrated in FIG. 2. The sugar chain labeled with 2AB was detected.

In FIG. 2, peaks 5 represent the peak derived from neutral sugar, and peaks 6 represent the peak derived from acidic sugar chain.

Exemplary Experiment 3

Figure 3:
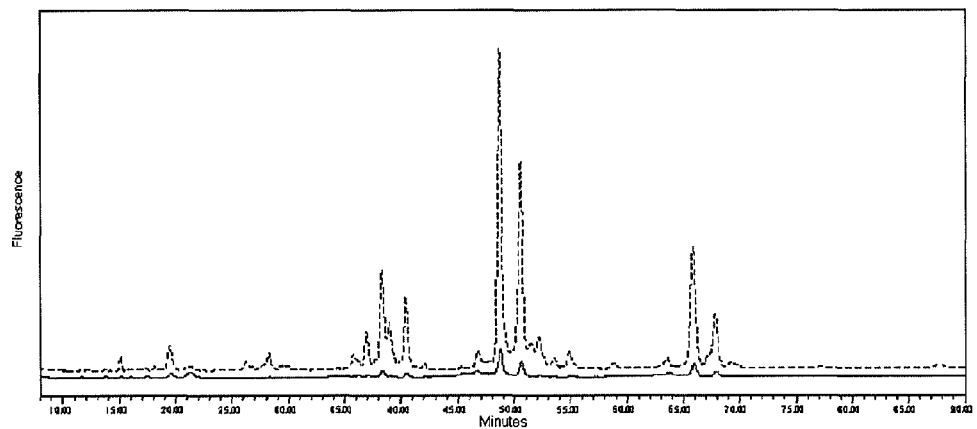
FIG. 3 is a chart illustrating a result of 2-AB labeled sugar chain of bovine fetuin obtained in Exemplary example 3, which was measured by high-performance liquid chromatography.

The exemplary experiment 3 was conducted similarly to Model Experiment 1, except that Affigel Hz (from BIO-RAD, 153-6047) was used as the beads having hydrazide group which serve as a carrier for trapping the sugar chains. Amount of use of Affigel was 50 µL. Results of measurement are illustrated in FIG. 3. In the chart, a solid line corresponds to Affigel, and a broken line corresponds to BlotGlyco(R) used in the exemplary experiment 1. It was found that the sugar chain labeled with 2AB was detected also by using Affigel Hz, while being characterized by with a lower intensity as compared with the case where BlotGlyco(R) was used.

The invention claimed is:

1. A method of labeling a sugar chain, used for labeling a sugar chain contained in a biological sample, comprising:
   (a) trapping a sugar chain in a sugar-trapping substance, which is a substance for specifically trapping a sugar chain from a biological sample;
   (c) releasing the sugar chain from said sugar-trapping substance; and
   (d) labeling the released sugar chain,
   wherein the processes (a), (c) and (d) are conducted sequentially in a single reaction vessel and in said processes (d), the sugar chain is labeled with a compound having amino group and the labeling of the sugar chain with said compound is carried out by reductive amination.

2. A method of labeling a sugar chain, used for labeling a sugar chain contained in a biological sample, comprising:
   (a) trapping a sugar chain in a sugar-trapping substance, which is a substance for specifically trapping a sugar chain from a biological sample;
   (b) washing said sugar-trapping substance having the sugar chains trapped thereon;
   (c) releasing the sugar chain from said sugar-trapping substance; and
   (d) labeling the released sugar chain,
   wherein the processes (a), (b), (c) and (d) are conducted sequentially in a single reaction vessel and in said processes (d), the sugar chain is labeled with a compound having amino group and the labeling of the sugar chain with said compound is carried out by reductive amination.

3. The method of labeling a sugar chain as claimed in claim 1,
   wherein in said process (a), said sugar-trapping substance is a carrier having a functional group for specifically reacting with an aldehyde group of the sugar chain.

4. The method of labeling a sugar chain as claimed in claim 3,
   wherein said functional group is a hydrazide group or an aminoxy group.

5. The method of labeling a sugar chain as claimed in claim 4,
   wherein said sugar-trapping substance has a crosslinking polymer structure represented by formula 1:

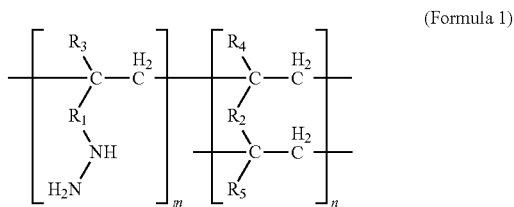

(Formula 1)

(wherein each of $R_1$ and $R_2$ represents a hydrocarbon chain having 1 to 20 carbon atoms which may be interrupted with —O—, —S—, —NH—, —CO— or —CONH—; each of $R_3$, $R_4$ and $R_5$ represents H, $CH_3$, or a hydrocarbon chain having 2 to 5 carbon atoms, Each of m and n represents the number of monomer units.

6. A method of labeling a sugar chain as claimed in claim 5,
   wherein said sugar-trapping substance has a crosslinking polymer structure represented by formula 2:

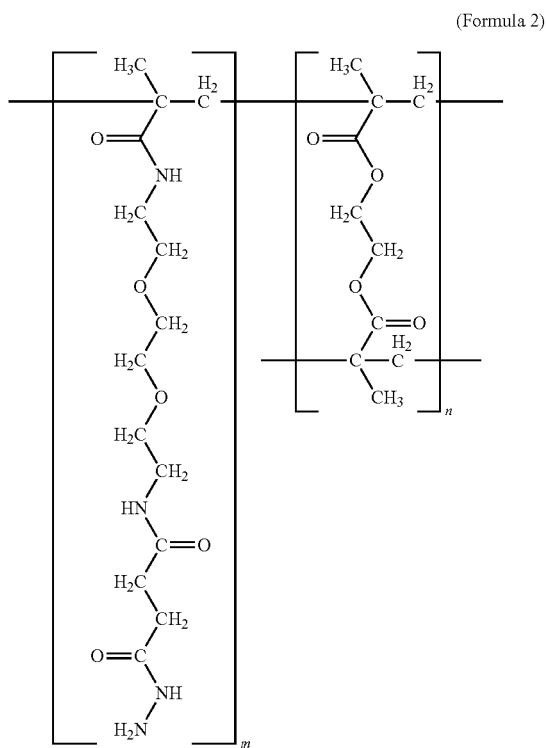

(Formula 2)

wherein each of m and n represents the number of monomer units.

7. The method of labeling a sugar chain as claimed in claim 1,
wherein said process (c) has a process of applying acid treatment to said sugar-trapping substance.

8. The method of labeling a sugar chain as claimed in claim 1,
wherein said processes (a) and (c) include a process of evaporating a reaction solvent.

9. The method of labeling a sugar chain as claimed in claim 1,
wherein said compound having amino group has UV-visible absorption characteristics or fluorescent characteristics.

10. The method of labeling a sugar chain as claimed in claim 1,
wherein said compound having amino group is at least one selected from 8-aminopyrene-1,3,6-trisulfonate, 8-aminonaphthalene-1,3,6-trisulphonate, 7-amino-1,3-naphtalenedisulfonic acid, 2-amino-9(10H)-acridone, 5-aminofluorescein, dansyl ethylenediamine, 2-aminopyridine, 7-amino-4-methylcoumarine, 2-aminobenzamide, 2-aminobenzoic acid, 3-aminobenzoic acid, 7-amino-1-naphthol, 3-(acetylamino)-6-aminoacridine, 2-amino-6-cyanoethylpyridine, ethyl p-aminobenzoate, p-aminobenzonitrile, or 7-aminonaphthalene-1,3-disulfonic acid.

11. A method of detecting a sugar chain comprising:
detecting a sugar chain labeled by the method of labeling a sugar chain as claimed in claim 1.

12. A method of fractionating a sugar chain comprising:
fractionating a sugar chain labeled by the method of labeling a sugar chain as claimed in claim 1.

* * * * *